United States Patent [19]

Coppa et al.

[11] Patent Number: 4,664,516
[45] Date of Patent: May 12, 1987

[54] METHOD OF AND APPARATUS FOR THE MEASUREMENT OF THE REFRACTIVE-INDEX PROFILE IN MONOMODE OPTICAL FIBRES

[75] Inventors: Gianni Coppa, Asti; Pietro Di Vita, Turin, both of Italy

[73] Assignee: Cselt - Centro Studi E E Laboratori Telecommunicazoni SpA, Turin, Italy

[21] Appl. No.: 779,082

[22] Filed: Sep. 20, 1985

[30] Foreign Application Priority Data

Dec. 18, 1984 [IT] Italy ............................. 68256 A/84

[51] Int. Cl.⁴ .................... G01N 21/47; G02B 27/42
[52] U.S. Cl. ............................... 356/73.1; 350/162.12
[58] Field of Search .......................... 356/73.1, 128; 350/162.11, 162.12

[56] References Cited

U.S. PATENT DOCUMENTS 4,515,475 5/1985 Payne .................................. 356/73.1

OTHER PUBLICATIONS

Article entitled, "A New Technique for Measuring the Refractive Index Profiles of Graded Optical Fibers'-'-W. J. Stewart-pp. 395-398.

10th European Conference on Optical Communication-Sep. 3-6, 1984-Liederhalle Stuttgart, Federal Republic of Germany.

Fourth International Conference on Integrated Optics and Optical Fiber Communication, Jun. 27-30, 1983-pp. 38-39.

"Spot-Size Measurements in Single-Mode Fibres"-R. Caponi et al., pp. 37-40.

Primary Examiner—Gene Wan
Attorney, Agent, or Firm—Karl F. Ross; Herbert Dubno

[57] ABSTRACT

The refractive-index value is obtained by radially scanning a near-field image of the fiber output face and by computing, for each image point, the ratio between a first intensity value, obtained in the presence of a mask, having a transmissivity proportional to the fourth power of the transversal beam coordinate and located in a far-field plane, and a second intensity value, obtained in the absence of such a mask. An automated measurement apparatus for implementing the method is also provided.

13 Claims, 6 Drawing Figures

METHOD OF AND APPARATUS FOR THE MEASUREMENT OF THE REFRACTIVE-INDEX PROFILE IN MONOMODE OPTICAL FIBRES

FIELD OF THE INVENTION

The present invention relates to optical fibres and, more particularly, to a method of and an apparatus for determining the refractive-index profile in monomode fibers.

BACKGROUND OF THE INVENTION

To determine the refractive-index profile in optical fibres the so-called near-field technique is generally used; this technique gives fairly accurate results without requiring any particular fiber preparation or sophisticated measurement apparatus.

According to this technique, a fiber end is illuminated and power distribution is examined at the opposite end by a suitable detector. According to whether lost power or guided power are measured there are two types of near-field techniques known as the "refracted nearfield" or the "bound near field" technique respectively.

The refracted near-field technique has been suggested by W. J. Stewart in the paper "A new technique for measuring the refractive index profile of graded optical fibres", presented at the 1977 International Conference on Integrated Optics and Optical Fibre Communication" (IOOC'77), Tokyo, 18–20 July 1977, paper C 2—2, pages 395-398.

The disadvantages of this method are that it does not exploit fiber propagation characteristics and the measurement is not carried out at the wavelengths used for the transmission once the fiber has been installed; as to the latter point, it is worth noting that the refractive index varies with the wavelength (refractive-index profile dispersion) and this dispersion is seldom accurately known, so that it can be difficult to obtain the profile at the operational wavelength.

An example of the bound near-field technique is described by G. Coppa, P. Di Vita and U. Rossi in the paper "A simple technique for the measurement of the refractive-index profile of monomode fibres" presented at the Fourth International Conference on Integrated Optics and Optical Fibre Communication, Tokyo, June 27-30, 1983, paper 28 S A2—2, pages 38-39.

The method described is based on the fact that the near-field intensity transmitted by a monomode fiber is proportional to the square of a transverse electromagnetic field component E satisfying the wave equation:

$$\Delta E + [k^2 n^2(r) - \beta^2] \cdot E = 0 \qquad (1)$$

where $k = 2\pi/\lambda$ = wave number in vacuum; $n(r)$ = refractive index at distance r from the fiber axis; $\beta$ = longitudinal mode propagation constant, and $\Delta$ = Laplacian operator. The value of $n(r)$ can be extracted by inverting the said wave equation.

This method can give inaccurate results since it requires complex mathematical calculations (for example, the digital calculation of a second derivative) which can cause errors and must be carried out on a measured quantity, which in turn can be error-affected.

OBJECT OF THE INVENTION

The present invention has as its object to provide a method which is still based on the bound near field technique so as to exploit the fiber propagation characteristics, and requires no complex processing of a measured value.

SUMMARY OF THE INVENTION

The method is characterized in that the radial scanning of an image of the fiber output end is effected, and for each value of the distance r from the image axis, two image-intensity measurements are effected, the first being carried out by optically filtering the beam emerging from the fiber so as to modulate the beam according to a factor $p^4$ (with $p = a \cdot \sin \theta$, $\theta$ being the angular beam coordinate, and a the distance of the generic filter point from the fiber output end), the second measurement being effected by directly collecting the beam outgoing from the fiber end, the refractive index value at that point being derived from the ratio between the first and the second measurements.

In fact it is known that far-field light power distribution depends on $|\widetilde{E}|^2$, where $\widetilde{E}$ is the bidimensional Fourier transform of field component E.

If the beam outgoing from the fiber is filtered with a circularly-symmetric mask with transmissivity distribution proportional to $p^4$, when the fiber output-face image is formed (which corresponds to antitransforming), the intensity in the image plane is proportional to $|\Delta E|^2$, as can be seen by calculating the Fourier bidimensional transform of function $p^4 \cdot |\widetilde{E}|^2$.

From the ratio between said measurement and that without mask (which as said gives $E^2$), for each point of the image the expression $[k^2 n^2(r) - \beta^2]^2$ is derived, as can be immediately deduced from (1). Since k is known, $n(r)$ is obtained, apart from an additive constant which has no influence in most applications and anyway depends on the cladding refractive index, which is generally known.

The mask can be a circularly-symmetrical grey distribution, with the above mentioned transmissivity distribution. A mask of this kind can be made by photographic methods.

As an alternative, a mask can be used with perfectly transparent and perfectly opaque zones bounded by pairs of spiral arcs of the type $\theta = \text{const} \cdot r^4$ or by spiral arcs and straight-line segments. In such a case the mask is to be rotated around its axis, with a rotation period equal to, or submultiple of, or much shorter than the total measurement duration, so as to allow a correct integration. If the mask rotation is not desired, the scanning can be made by selecting on the image plane a number of illuminated annuli of different radii and by measuring the total power by which they are traversed. With respect to radial image scanning with rotating mask, this method has the advantage of a greater intensity of the measured signal and hence of a better signal-to-noise ratio.

The use of masks with radially varying transmissivity is known for spot-size measurements in single-mode fibers (see e.g. Caponi et al. "Spot-size measurements in single-mode fibres", Symposium on Optical Fiber Measurements, Boulder, USA, Oct. 2-3, 1984, and W. J. Stewart et al., "Waveguide dispersion measurement in monomode fibres from spot size", 10th European Conference on Optical Communications, Stuttgart, Sept. 3-6, 1984). Yet these measurements are of an integral type, i.e. they require the determination of the total beam intensity on the measurement plane, and the quality of the image and even its formation is of slight importance.

In the present case, on the contrary, it is always necessary to form a near-field image, and its quality is important, because the optical system allowing the image formation affects its Fourier transform.

On the other hand, spot-size determination requires the modulation by a factor $p^2$ and not by a factor $p^4$; modulation by a factor of this kind in the systems described by Caponi et al. and Stewart et al. would supply values of a fourth order moment of the electromagnetic field associated with the beam and such moment gives no information on refractive index profile.

In addition, even if a radial scanning of a near-field image in refractive-index profile measurement systems is known, e.g. from the paper by Coppa et al., such a scanning is to be followed, as mentioned, by complex processings of measurement results, which processings give reliable results only if the measurement is highly accurate. This precision is not required by the method provided by the present invention, which in addition directly supplies refractiveindex values as a simple ratio between two measurements.

BRIEF DESCRIPTION OF THE DRAWING

The invention will become clearer with reference to the annexed drawing in which.

SPECIFIC DESCRIPTION

Figure 1:
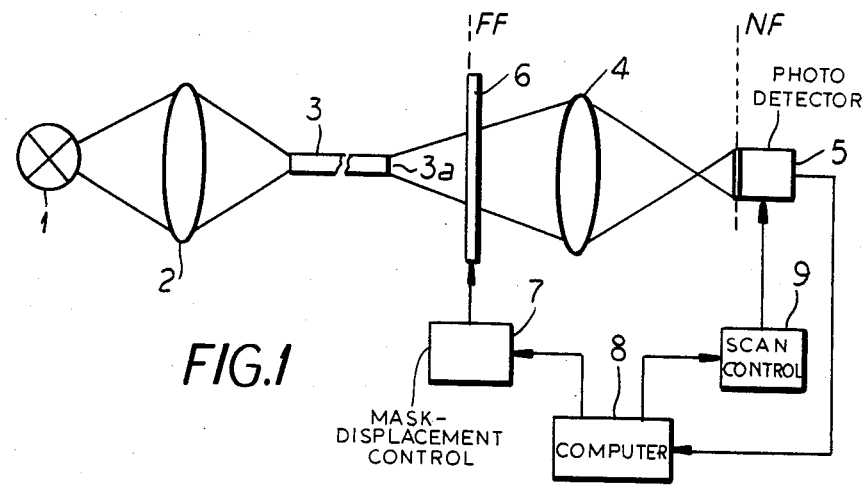
FIG. 1 is a schematic representation of the apparatus according to the invention.

As shown in FIG. 1, a light source 1 emits a beam which, through launching optics 2, is sent into a monomode fiber 3, whose refractive-index profile is to be determined.

The beam outgoing from fiber 3 is collected by an optical system 4 which forms an image of the output face 3a of the fiber on a plane NF. On the latter, the sensitive surface of a photodetector 5 (photodiode, telecamera, fiber tail end etc.) is arranged, this detector being adapted to radially scan said image.

A mask or spatial filter 6 can be located coaxially to the beam on a far-field plane, between fiber output 3a and optical system 4, to modulate the beam intensity proportionally to $p^4$, p being the transverse beam coordinate. Mask 6 is mounted on a support, not shown, which is displaced by a convenient control system, schematized by block 7, to allow the insertion of mask 6 on or the removal from the beam trajectory.

Detector 5 is followed by a measuring and computing system 8, which, for each scanning point, measures the light intensity of the image in presence or absence of mask 6, calculates the ratio between the two measured values and obtains the refractive index n(r) starting from the square root of such ratio. More particularly, the square root of the ratio gives the expression $k^2 n^2(r) - \beta^2$, wherefrom n(r) is immediately derived.

For each position of detector 5, device 7 shifts the support of mask 6 first to place mask 6 on the trajectory of the beam outgoing from fiber 3 and then to remove the mask from said trajectory.

Advantageously the apparatus is automated. To obtain that, measuring and computing system 8 can be part of a processor which is connected to control devices 7 of the support of mask 6 and to the scanning control devices (schematized by block 9) and controls the displacements of said devices in the way described.

The image intensity, after the filtering with mask 6, is really proportional to $(\Delta E)^2$ provided the mask is circularly symmetric; otherwise, an intensity information relative to a whole image circumference is required.

Figure 2:
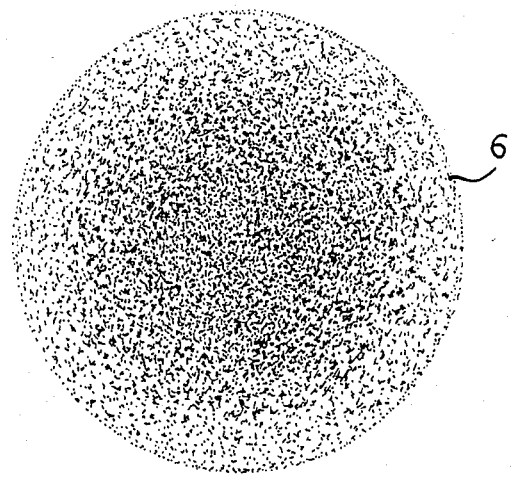
FIGS. 2 and 3 are examples of filtering masks.

A circularly symmetric mask can consist of a grey distribution whose transmissivity is null at the center and maximum at the edges and varies with the law mentioned above. Such a mask can be implemented with photographic techniques. An example is given in FIG. 2.

Figure 3:
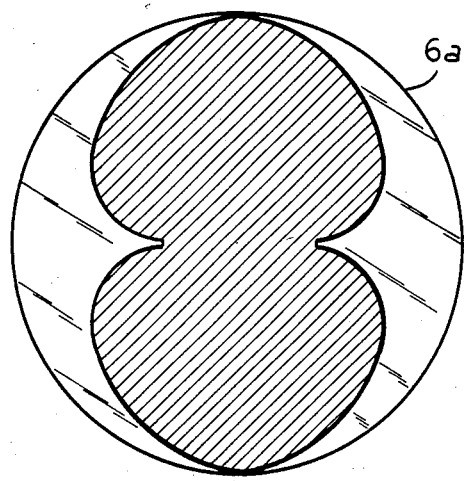

An asymmetrical mask can on the contrary consist of perfectly opaque and perfectly transparent sectors, each bound by two spiral arcs of the type $\theta = \cos t \cdot r^4$ or by a spiral arc and a straight line segment, such that the transmittivity along any annulus of radius r is proportional to $r^4$. An example is shown by mask 6a in FIG. 3.

Figure 4:
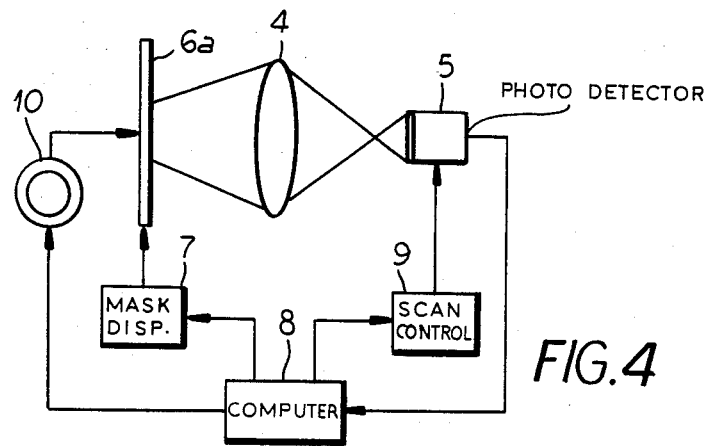
FIG. 4 is a schematic partial representation of a variant.

To allow detector 5 to supply the information relevant to a whole circumference, mask 6a is caused to rotate around its axis, so that it accomplishes either one turn or an integer number of turns while remaining inserted along the beam trajectory. This entails an auxiliary motor associated with mask 6 (FIG. 4) to control its rotation on the support. Also such a motor can be started by the processor.

Figure 5:
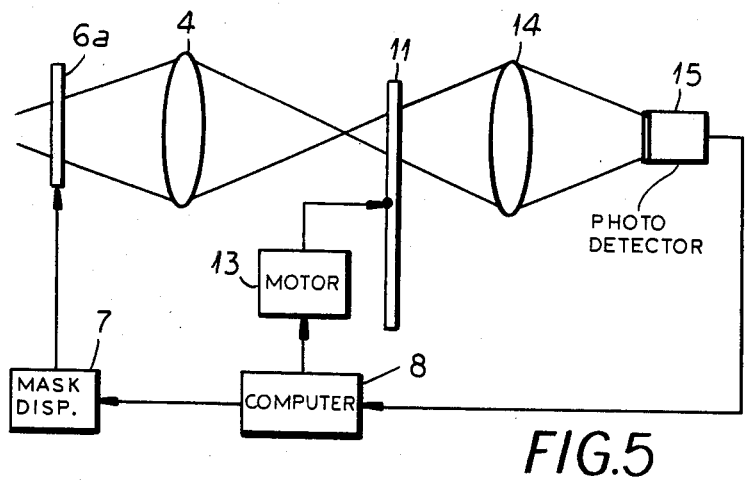
FIG. 5 is a schematic partial representation of a second variant.

If rotation of mask 6 is not desired, the information of the illumination relative to a whole circumference can be obtained by the arrangement of FIG. 5.

Figure 6:
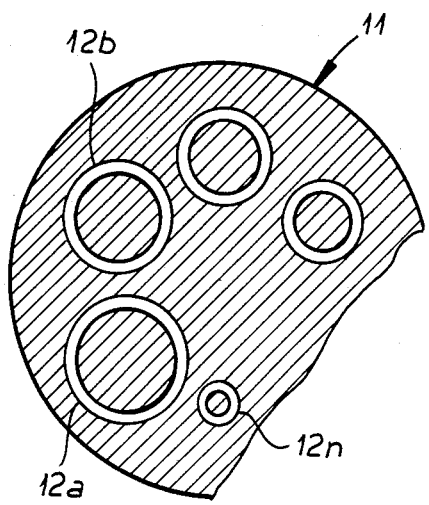
FIG. 6 shows a detail of FIG. 5.

On the near-field plane there is a disc 11 presenting a plurality of transparent annuli 12a, 12b, ... 12n (FIG. 6), of different dimeters, whose centers lie on a same circumference.

Disc 11 is associated with motor 13 and is mounted on a support allowing its step-by-step rotation around an axis passing through the centre of the above circumference, so that the beam axis at each step passes through the center of an annulus 12. An optical system 14 located past disc 11 focuses the beam outgoing from an annulus on a fixed detector 15, connected to measuring system 8. In this case too motor 13 can be controlled by the processor which measurement and computing system 8 belongs to, to automate the system.

Diameter difference among the various annuli 12 basically corresponds to a step of the radial scanning carried out by detector 5 in the embodiment of FIG. 1.

We claim:

1. A method of determining the refractive index profile in a monomode fiber, in which an image of a fiber output face is formed and a radial scanning of said image is effected, said method comprising for each value of distance from the image axis, effecting two image intensity measurements, a first image measurement being obtained by spatially filtering the beam outgoing from the fiber in a farfield plane, so as to modulate the beam according to a factor proportional to the fourth power of the transverse beam coordinate in said far-field plane, the second image measurement being effected by directly collecting the beam outgoing from the fiber, and obtaining the refractive-index value at the measurement point from the ratio between the first and second measurements.

2. The method defined in claim 1 wherein the refractive-index value at a point is obtained from the square root of such a ratio.

3. The method defined in claim 1 wherein said spatial filtering is implemented by using a circularly symmetric mask consisting of a grey distribution where the transmissivity is null at the center and maximum at the edges.

4. The method defined in claim 1 wherein said spatial filtering is implemented by using a circularly asymmetric mask with transparent and opaque zones, arranged so that the mask is opaque in correspondence with the beam axis while the ratio between the surface of the two kinds of zones, at a distance r from the axis, is proportional to $r^4$, and rotating said mask around its axis with such a speed that it accomplishes an integral number n of turns (n>1) during the time period corresponding to the first measurement, so as to allow a correct integration of the signal measured.

5. The method defined in claim 1 wherein said spatial filtering is implemented by using a circularly asymmetric mask with transparent and opaque zones, arranged so that the mask is opaque in correspondence of the beam axis, while the ratio between the surfaces of the two types of zones, at a distance r from the beam axis, is proportional to $r^4$, and in that for said radial scanning of the image a number of annuli with different radii are selected in the image itself, said two measurements being effected for each annulus.

6. An apparatus for determining the refractive index profile of a monomode fiber by forming an image of a fiber output face and radially scanning said image, said apparatus comprising:
   an optical beam source;
   a first optical system for transferring the beam to an optical fiber;
   a second optical system for transferring the beam outgoing from the fiber onto an image plane;
   a photodetector which radially scans the image and supplies electrical signals representing the image intensity;
   a measuring and computing system which obtains the refractive index values from such electrical signals; and
   a spatial filter which modulates, on a far-field plane, the intensity of the beam outgoing from the fiber according to a factor proportional to the fourth power of the transverse beam dimension in said far-field plane, and is mounted on a support movable between a first position, in which said filter intercepts the beam outgoing from the fiber, and a second position, where the filter is shifted from the trajectory of such a beam, said detector, for each position of said radial scanning, supplying a first intensity value in the presence of the filter and a second intensity value in the absence of said filter, the measuring and computing system obtaining the value of the refractive index, for that position, from a ratio between the first and the second intensity values.

7. The apparatus defined in claim 6 wherein a processor comprising said computing system controls the scanning and the operation of the support of the filter, so as to cause said support to displace in synchronism with the scanning.

8. The apparatus defined in claim 6 wherein said filter consists of a circularly symmetric mask with null transmissivity at the center and maximum transmissivity at the edges.

9. The apparatus defined in claim 6 wherein said filter consists of a circularly asymmetric mask, comprising opaque and transparent sectors such that the transmissivity along an annulus of radius r is proportional to $r^4$.

10. The apparatus defined in claim 7 wherein said filter is mounted on said support so as to be rotatable around its axis, and is associated with a motor which, while said support is in its first position, causes the rotation of the filter so that it performs an integral number n (n>1) of turns.

11. The apparatus defined in claim 10 wherein said motor is controlled by the processor controlling the displacement of the support of the filter and is started by said processor automatically, when the support of the filter is in said first position.

12. The apparatus defined in claim 7 wherein said filter is fixedly mounted on the support, and in that for said radial scanning, an opaque element is located in said image plane, which element is rotatable around an axis parallel to the beam axis, presents a series of angularly spaced transparent annuli, and is associated with a motor which controls its rotation around said axis, so that it sequentially arranges said transparent annuli coaxially to the beam.

13. The apparatus defined in claim 12 wherein the motor actuating said opaque element is controlled by the same processor which controls the means actuating the support of the filter, so that actuating means cause the displacement of the support from said second position to the first and vice versa for ach step of the rotation of the opaque element.

* * * * *